US008003818B2

(12) United States Patent
Van Den Brink et al.

(10) Patent No.: US 8,003,818 B2
(45) Date of Patent: Aug. 23, 2011

(54) PROCESS FOR THE HYDROGENATION OF A LACTONE OR OF A CARBOXYLIC ACID OR AN ESTER HAVING A GAMMA-CARBONYL GROUP

(75) Inventors: Peter John Van Den Brink, Amsterdam (NL); Klaas Lambertus Von Hebel, Amsterdam (NL); Jean-Paul Lange, Amsterdam (NL); Leonardus Petrus, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1025 days.

(21) Appl. No.: 11/314,404

(22) Filed: Dec. 21, 2005

(65) Prior Publication Data

US 2006/0162239 A1 Jul. 27, 2006

(30) Foreign Application Priority Data

Dec. 23, 2004 (EP) .................................... 04106969

(51) Int. Cl.
*C07C 69/34* (2006.01)
*C07C 69/52* (2006.01)

(52) U.S. Cl. ........................................................ 560/190

(58) Field of Classification Search .................. 568/861; 560/231, 179; 561/1
See application file for complete search history.

(56) References Cited

U.S. PATENT DOCUMENTS

| | | | | |
|---|---|---|---|---|
| 3,849,457 | A * | 11/1974 | Haag | 560/8 |
| 3,968,294 | A | 7/1976 | Robitschek et al. | |
| 4,048,196 | A * | 9/1977 | Broecker et al. | 549/508 |
| 4,301,077 | A * | 11/1981 | Pesa et al. | 549/508 |
| 4,594,130 | A | 6/1986 | Chang et al. | |
| 4,652,685 | A * | 3/1987 | Cawse et al. | 568/864 |
| 4,797,382 | A * | 1/1989 | De Thomas et al. | 502/245 |
| 4,885,411 | A * | 12/1989 | De Thomas et al. | 568/864 |
| 4,904,342 | A | 2/1990 | Arnoldy et al. | |
| 5,068,105 | A | 11/1991 | Lewis et al. | |
| 5,456,964 | A | 10/1995 | Tamura et al. | |
| 5,596,113 | A * | 1/1997 | Douglas et al. | 556/14 |
| 5,608,105 | A | 3/1997 | Fitzpatrick | |
| 5,614,564 | A | 3/1997 | Hwang et al. | |
| 5,883,266 | A | 3/1999 | Elliott et al. | 549/273 |
| 5,892,107 | A * | 4/1999 | Farone et al. | 562/515 |
| 6,054,611 | A * | 4/2000 | Farone et al. | 562/515 |
| 6,527,914 | B1 | 3/2003 | Shevchenko et al. | |
| 6,894,199 | B2 * | 5/2005 | Heikkila et al. | 568/864 |
| 2002/0069987 | A1 | 6/2002 | Pye | |
| 2004/0224902 | A1 | 11/2004 | Shukla et al. | |
| 2004/0231810 | A1 | 11/2004 | Rouso et al. | |
| 2005/0221078 | A1 | 10/2005 | Lu et al. | |
| 2006/0135793 | A1 | 6/2006 | Blessing et al. | |
| 2006/0162239 | A1 | 7/2006 | Van Den Brink et al. | |
| 2007/0034345 | A1 | 2/2007 | Petrus et al. | |
| 2007/0100162 | A1 | 5/2007 | Petrus et al. | |

FOREIGN PATENT DOCUMENTS

| | | | |
|---|---|---|---|
| EP | 0069409 | | 1/1983 |
| EP | 69409 | | 11/1985 |
| EP | 472474 | | 1/1996 |
| EP | 1036878 | | 9/2000 |
| GB | 1240580 | | 7/1971 |
| GB | 2040275 | A | 8/1980 |
| JP | 05140323 | | 6/1993 |
| JP | 7-18269 | | 1/1995 |
| JP | 09059519 | | 3/1997 |
| JP | 11029647 | | 2/1999 |
| WO | 82/00483 | | 2/1982 |
| WO | 98/26869 | | 6/1998 |
| WO | 99/65851 | | 12/1999 |
| WO | 01/59202 | A2 | 8/2001 |
| WO | 02/074760 | | 9/2002 |
| WO | WO 02085833 | * | 10/2002 |
| WO | 2003/014231 | A1 | 2/2003 |
| WO | 2005/058856 | A1 | 6/2005 |
| WO | 2005/059016 | A1 | 6/2005 |

OTHER PUBLICATIONS

Wan et al., Ruthenium(II)-sulfonated BINAP: a novel water-soluble asymmetric hydrogenation catalyst, Tetrahedron: Asymmetry (1993), 4(12), 2461-2468.*

Behr et at., Aqueous biphasic catalysis as a powerful tool for catalyst recycling in telomerization and hydrogenation chemistry, Green Chemistry (2003), 5(2), 198-204.*

Fabre et al., Catalytic Hydrogenation of Arabinonic Acid and Lactones to Arabitol, Journal of Catalysis (2002), 208(1), 247-254.*

Henin et al., {Enantioselective photodeconjugation of conjugated esters and lactones in the presence of ephedrine, Tetrahedron (1989), 45(19), 6171-96}.* Melikyan et al., {Low-molecular-weight bioregulators. III. Synthesis of 4E-tridecenyl acetate, the sex pheromone of *Keiferia lycopersicella*, Khimiya Prirodnykh Soedinenii (1990), (1), 102-6}.*

European Patent Office Search Report dated Jun. 22, 2005, Application No. 04106969.1.

Kirk-Othmer's Encyclopedia of Chemical Technology, 3rd ed., 1981, vol. 13, p. 909.

Ullmann's Encyclopedia of Industrial Chemistry, 5th ed., 1990, vol. A15, p. 80.

Smook, Handbook for Pulp and Paper Technologies, Angus Wilde Publications, 2nd edition, p. 333., 1992.

(Continued)

*Primary Examiner* — Daniel Sullivan
*Assistant Examiner* — Jennifer Cho Sawyer

(57) ABSTRACT

The invention provides a process for the hydrogenation of a reactant selected from the group consisting of: at the ring-closing carbon atom and has a proton at a (a) a 5- or 6-membered lactone that is substituted carbon atom adjacent to the ring-closing carbon atom;

(b) an ester of a carboxylic acid having a gamma-carbonyl group and a proton at a carbon atom adjacent to the carbon atom of the carbonyl group; and (c) a carboxylic acid having a gamma-carbonyl group and a proton at a carbon atom adjacent to the carbon atom of the carbonyl group, wherein the reactant is contacted with a strongly acidic heterogeneous catalyst comprising a hydrogenating metal, in the presence of hydrogen, at a temperature in the range of from 100 to 350° C. and a pressure in the range of from 1 to 150 bar (absolute).

The invention further provides a fuel composition, preferably a diesel composition, comprising di-alkyl 4-methyl-nonanedioate or di-alkyl 3-ethyl-4-methylheptanedioate.

6 Claims, No Drawings

OTHER PUBLICATIONS

Copending U.S. Appl. No. 11/420,981 (United States Publication No. US2007/00034345 A1), 2007.
Copending U.S. Appl. No. 11/582,888 (United States Publication No. US2007/0100162 A1), 2007.
Heitz et al., "Solvent Effects on Liquefaction: Solubilization Profiles of a Canadian Prototype Wood, *Populus deltoides*, in the Presence of Different Solvents", Can. J. Chem. Eng., 72:1021-1027, Dec. 1994.
Yamada, "Rapid Liquefaction of Lignocellulosic Waste by Using Ethylene Carbonate" Biores. Technol., 70:61-67,1999.
European Search Report for Application No. 03 25 7858, 2009.
Leonard, H., "Levulinic Acid as a Basic Chemical Raw Material," Newport Industries, Inc., Pensacola, Florida, 48(6):1331-1341, Aug. 1956.

* cited by examiner

PROCESS FOR THE HYDROGENATION OF A LACTONE OR OF A CARBOXYLIC ACID OR AN ESTER HAVING A GAMMA-CARBONYL GROUP

CROSS-REFERENCE TO RELATED APPLICATIONS

This application claims priority from European Patent Application No. 04106969.1, filed on Dec. 23, 2004, which is incorporated herein by reference.

FIELD OF THE INVENTION

The present invention provides a process for the hydrogenation of a reactant selected from the group consisting of:

(a) a 5- or 6-membered lactone that is substituted at the ring-closing carbon atom and has a proton at a carbon atom adjacent to the ring-closing carbon atom;

(b) an ester of a carboxylic acid having a gamma-carbonyl group and a proton at a carbon atom adjacent to the carbon atom of the carbonyl group; and (c) a carboxylic acid having a gamma-carbonyl group and a proton at a carbon atom adjacent to the carbon atom of the carbonyl group.

The present invention further provides a fuel composition comprising di-alkyl 4-methylnonanedioate or di-alkyl 3-ethyl-4-methylheptanedioate. Di-alkyl 4-methylnonanedioate and di-alkyl 3-ethyl-4-methylheptanedioate are esters obtainable by the process according to the invention.

BACKGROUND OF THE INVENTION

It is known that levulinic acid or its esters can be converted into gamma-valerolactone (γ-valerolactone)

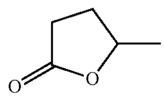

by catalytic hydrogenation. The conversion may proceed via hydrogenation to 4-hydroxy pentanoic acid followed by (trans)esterification to γ-valerolactone or via (trans)esterification of the enol form of levulinic acid to Angelica lactone followed by hydrogenation to γ-valerolactone. γ-valerolactone may be further hydrogenated, via 1,4-pentadiol, into methyl tetrahydrofuran (MTHF). Processes for the conversion of levulinic acid into γ-valerolactone are for example disclosed in U.S. Pat. No. 5,883,266, WO 02/074760 and WO 98/26869. A process for the catalytic hydrogenation of levulinate esters to form γ-valerolactone is disclosed in EP 069 409 A1.

γ-valerolactone is known to be a very stable compound that is, starting from levulinic acid or its esters, more easily formed under catalytic hydrogenating conditions than non-cyclic hydrogenated compounds such as pentanoic acid or pentanoates. Due to its high stability, it is difficult to convert the thus-formed γ-valerolactone into pentanoic acid or a pentanoate. In general, it is difficult to open 5- or 6-membered lactone rings, in particular 5-membered lactone rings.

There is a need for a process for the hydrogenation of γ-valerolactone, levulinic acid or its esters into pentanoic acid or pentanoates in sufficiently high yield. Such pentanoates could be advantageously used as bio-derived compounds in transportation fuels in particular diesel fuel.

SUMMARY OF THE INVENTION

It has now been found that it is possible to convert a 5- or 6-membered lactone that is substituted at the ring-closing carbon atom into a non-cyclic hydrogenated compound by contacting the lactone, in the presence of hydrogen and at elevated temperature, with a bi-functional catalyst, i.e., a strongly acidic catalyst with a hydrogenating compound. It has also been found that carboxylic acids or esters that easily form such lactones under these process conditions, i.e., at elevated temperature and in the presence of hydrogen and a bi-functional catalyst, can also be hydrogenated to non-cyclic hydrogenated compounds by contacting them with a bi-functional catalyst, in the presence of hydrogen and at elevated temperature.

Accordingly, the present invention provides a process for the hydrogenation of a reactant selected from the group consisting of:

(a) a 5- or 6-membered lactone that is substituted at the ring-closing carbon atom and has a proton at a carbon atom adjacent to the ring-closing carbon atom;

(b) an ester of a carboxylic acid having a gamma-carbonyl group and a proton at a carbon atom adjacent to the carbon atom of the carbonyl group; and (c) a carboxylic acid having a gamma-carbonyl group and a proton at a carbon atom adjacent to the carbon atom of the carbonyl group, wherein the reactant is contacted with a strongly acidic heterogeneous catalyst comprising a hydrogenating metal, in the presence of hydrogen, at a temperature in the range of from 100 to 350° C. and a pressure in the range of from 1 to 150 bar (absolute).

In the process according to the invention a reactant selected from a lactone, a carboxylic acid having a gamma-carbonyl (γ-carbonyl) group or its ester, is converted into a non-cyclic saturated carboxylic acid or ester. The non-cyclic saturated esters obtainable by the process according to the invention can be suitably used as fuel components, in particular in diesel. It is for example known that ethyl pentanoate may be used as a fuel additive. Reference is made to Derwent abstract No. 1995-094077, which is an English abstract of JP1995018269. It has been found that di-alkyl 4-methylnonanedioate

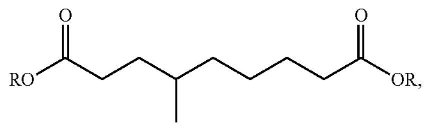

and di-alkyl 3-ethyl-4-methylheptanedioate,

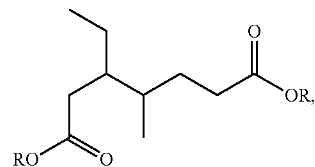

both esters that are obtainable by the process according to the invention, may be used as a fuel component.

Accordingly, the invention further provides a fuel composition comprising di-alkyl 4-methylnonanedioate or di-alkyl 3-ethyl-4-methylheptanedioate.

DETAILED DESCRIPTION OF THE INVENTION

In the process according to the invention, a reactant selected from (a) a lactone, (b) a carboxylic acid having a γ-carbonyl group and a proton at a carbon atom adjacent to the carbonyl group, and (c) an ester of such carboxylic acid, is hydrogenated by contacting the reactant at elevated temperature with a strongly acidic heterogeneous catalyst comprising a hydrogenating metal in the presence of hydrogen.

The lactone is a 5- or 6-membered lactone that is substituted at the ring-closing carbon atom and has a proton at a carbon atom adjacent to the ring-closing carbon atom. Such lactone has the general molecular formula (1)

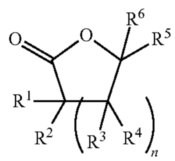

wherein n is 1 or 2, $R^1$, $R^2$, $R^3$, $R^4$, and $R^5$ each are, independently, a proton or an organic group that is connected with a carbon atom to the carbon atom on the ring structure, and $R^6$ is an organic group that is connected with a carbon atom to the ring-closing carbon atom. There needs to be a proton at a carbon atom adjacent to the ring-closing carbon atom. Thus, either $R^3$ or $R^4$ is a proton or any of $R^5$ and $R^6$ is an organic group that is connected with a proton-bearing carbon atom to the ring-closing carbon atom. In case of a 6-membered lactone, each of $R^3$ and $R^4$ at each carbon atom may differ from each other.

Preferably, $R^6$ is an alkyl group. $R^1$ to $R^5$ each are preferably a hydrogen atom. Examples of such preferred lactones are delta-hexanolactone (δ-hexanolactone)

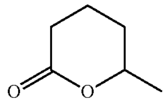

and γ-valerolactone

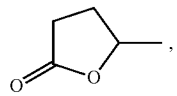

Preferably, the lactone is a 5-membered lactone.

Reference herein to a carboxylic acid having a γ-carbonyl group and a proton at a carbon atom adjacent to the carbon atom of the carbonyl group or an ester of such carboxylic acid is to a compound with the general molecular formula $$R^7OOC—CR^1R^2—CR^3R^4—CO—R^6 \qquad (2)$$

wherein $R^1$, $R^2$, $R^3$, $R^4$ and $R^6$ are as defined hereinabove and $R^7$ is a proton in the case of a carboxylic acid as reactant and an organic group that is connected with a carbon atom to the oxygen atom in case of an ester as reactant. Preferably, $R^3$ or $R^4$ is a proton. If the carbon atom of $R^6$ that is connected to the gamma carbon atom has a proton, $R^3$ or $R^4$ does not need to be a proton.

In the process according to the invention the reactant is contacted in the presence of hydrogen with a strongly acidic heterogeneous catalyst comprising a hydrogenating metal. The reactant is contacted with the catalyst at a temperature in the range of from 100 to 350° C. and a pressure in the range of from 1 to 150 bar (absolute).

In case the reactant is an ester, the ester is converted into its corresponding ester with two protons at the gamma carbon atom, i.e., an ester having the general molecular formula (3):

$$R^7OOC—CR^1R^2—CR^3R^4—CH_2—R^6 \qquad (3)$$

wherein $R^1$ to $R^4$ and $R^6$ and $R^7$ are as defined hereinabove.

In case the reactant is a carboxylic acid, the reactant is converted into its corresponding carboxylic acid with two protons at the gamma carbon atom, i.e., an acid having the general molecular formula (4):

$$HOOC—CR^1R^2—CR^3R^4—CH_2—R^6 \qquad (4)$$

In case the reactant is a lactone according to molecular formula (1), a carboxylic acid having the general molecular formula (5) is formed:

$$HOOC—CR^1R^2—(CR^3R^4)_n—CH_2—R^6 \qquad (5)$$

Thus, if the lactone reactant is γ-valerolactone, pentanoic acid

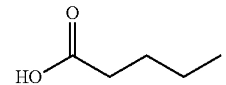

is formed.

In case of δ-hexanolactone as reactant, hexanoic acid

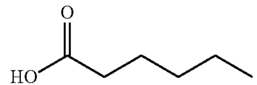

is formed.

If the desired product is an ester and the reactant is a lactone or a carboxylic acid, external alcohol may be added to the reactant in order to obtain an ester according to general molecular formula (3) or the ester of the acid according to general molecular formula (5). It is preferred that the amount of external alcohol does not exceed the stoichiometric amount, since excess alcohol could result in dialkyl ether formation and the concurrent formation of water.

Without wishing to be bound to any theory, it is believed that in the process according to the invention, the reactant ester or acid is first hydrogenated to form an ester or acid with a gamma hydroxyl group. The ester or acid with the gamma hydroxyl group is then converted into its gamma lactone by an internal (trans)esterification reaction. Under the conditions of the process according to the invention, ring-opening of the gamma lactone thus-formed or of the reactant lactone occurs. It is believed that the lactone is first converted into an unsaturated acid and then converted to the corresponding saturated acid (4) or (5). In case alcohol is present, either alcohol that is in-situ formed in a transesterification reaction or external alcohol, an ester according to molecular formula (3) or an ester of a carboxylic acid according to molecular formula (5) is formed.

A small amount of water will be present in the process according to the invention, due to water formation in elimination or (trans) esterification reactions that occur. If the reactant is an ester, the presence of water results in ester hydrolysis and, thus, in acid formation. The presence of acids is preferably minimized since it could result in some catalyst deactivation. Therefore, an ester reactant is preferred over an acid reactant.

Preferably, the reactant is a compound that is obtainable from biomass, in particular from cellulosic or lignocellulosic material. Examples of such compounds are γ-valerolactone, levulinic acid or an ester of levulinic acid ($R^6$ is a methyl group, $R^1$, $R^2$, $R^3$ and $R^4$ each are a hydrogen atom), a dimer of levulinic acid or a mono- or di-ester of such dimer. Examples of dimers of levulinic acid with a γ-carbonyl group are 4-methyl-6-oxononanedioic acid, 3-acetyl-4-methylheptanedioic acid, or their lactones, i.e., 5-(2-methyl-5-oxotetrahydrofuran-2-yl)-4-oxopentanoic acid or 3-(2-methyl-5-oxotetrahydrofuran-2-yl)-4-oxopentanoic acid. These dimers have molecular formulas (6), (7), (8) and (9), respectively:

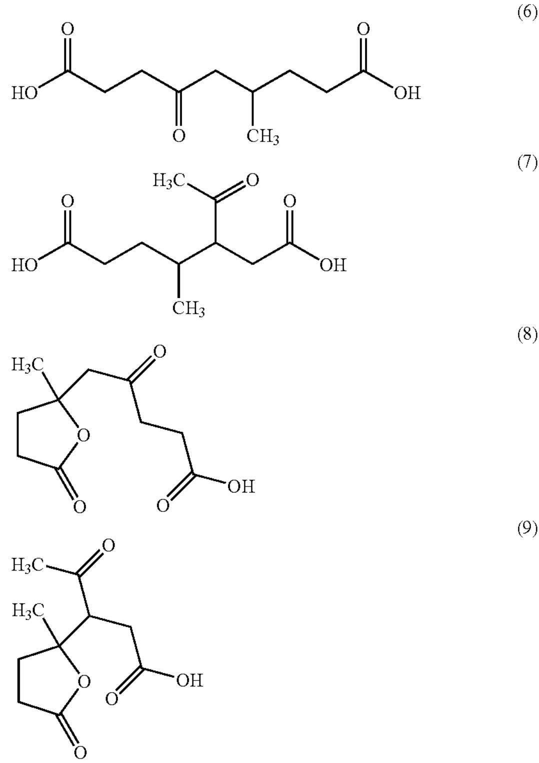

The levulinic acid dimers according to molecular formulas (6) to (9) may be obtained by contacting levulinic acid in the presence of hydrogen with a strongly acidic catalyst having a hydrogenating function, e.g., Pd/cation-exchange resin, at elevated temperature and preferably at elevated pressure. Typical process temperatures and pressures are in the range of from 60 to 170° C. and of from 1 to 200 bar (absolute), respectively. Such process for levulinic acid dimerization is described in detail in co-pending patent application EP 04106107.8. The catalyst and process conditions of this process are similar to those applied in the known single-step process for the production of methyl isobutyl ketone from acetone Such single-step methyl isobutyl ketone process is for example disclosed in Kirk-Othmer's *Encyclopedia of Chemical Technology*, 3rd ed., 1981, Vol. 13, p. 909, in Ullmann's *Encyclopedia of Industrial Chemistry*, 5th ed., 1990, Vol. A15, p. 80, and in WO 99/65851.

Particularly preferred reactants are esters of levulinic acid or esters of any one of the levulinic acid dimers according to molecular formulas (6) to (9). In case of the di-carboxylic acid according to molecular formula (6) or (7) the reactant is preferably a di-alkyl, more preferably a diethyl ester.

In the case that the reactant is an ester, it is preferably an alkyl ester ($R^7$ is an alkyl group), more preferably an alkyl ester with at most 10 carbon atoms in the $R^7$ group, (i.e., $R^7$=$C_{1-10}$ alkyl), even more preferably an ethyl ester.

If external alcohol is added to the reactants, it is preferably an alkyl alcohol, more preferably an alkyl alcohol with at most 10 carbon atoms, even more preferably at most 4 carbon atoms, most preferably is ethanol. The external alcohol may be a diol, such as for example ethylene glycol or butane-1,4-diol. In that case a di-ester comprising two carboxylic acid fragments and one alcohol fragment is formed.

The catalyst of the process according to the invention is a strongly acidic heterogeneous catalyst comprising a hydrogenating metal. Any solid strongly acidic catalytic material that is resistant to the process conditions applied may be used. Preferably, the catalyst comprises a strongly acidic zeolite, for example acidic zeolite beta or acidic ZSM-5. Such acidic zeolite may be bound with a binder, for example silica, alumina, acidic clays, titania or zirconia.

The catalyst further comprises a hydrogenating metal, preferably a metal of any one of groups 7 to 11 of the Periodic Table of Elements (latest IUPAC notation). More preferably the hydrogenating metal is Ni, Rh, Pd, Pt, Re, Ru or a combination of two or more thereof. Ni, Ru and Rh are particularly preferred hydrogenating metals. The concentration of the hydrogenating metal based on the total weight of the catalyst will typically be in the range of from 1 to 50 wt % for non-noble metals and in the range of from 0.05 to 5 wt % for noble metals. Preferred concentrations are from 2 to 20 wt % for non-noble metals and from 0.1 to 2 wt % for noble metals.

The catalyst may be a physical mixture of a strongly acidic heterogeneous catalyst and supported hydrogenating metal. Preferably, the catalyst comprises hydrogenating metal supported on the strongly acidic material.

The reactant is contacted with the catalyst at a temperature in the range of from 100 to 350° C., preferably of from 150 to 250° C. and at a pressure in the range of from 1 to 150 bar (absolute), preferably of from 20 to 100 bar (absolute), more preferably of from 50 to 80 bar (absolute).

The weight hourly velocity of the reactant will typically be in the range of from 0.01 to 10 kg reactant per kg catalyst per hour.

The ester formed by the process according to the invention, i.e. the ester according to formula (3) or the esters of the acids according to formulas (4) and (5), can be suitably used as a fuel component, in particular in diesel. In particular the esters formed by reacting gamma valerolactone, levulinic acid, or its esters or by reacting dimers of levulinic acid, such as 4-methyl-6-oxononanedioic acid, 3-acetyl-4-methylheptanedioic acid, their esters, or their lactones are suitable as fuel component. The resulting esters are in that case esters of pentanoic acid (gamma valerolactone, levulinic acid or its esters as reactant), di-esters of 4-methylnonanedioic acid (4-methyl-6-oxononanedioic acid, its lactone, or its (di)ester as reactant) or di-esters of 3-ethyl-4-methylheptanedioic (3-acetyl-4-methylheptanedioic acid, its lactone, or its (di) ester as reactant). The ethyl esters are particularly preferred as fuel component.

EXAMPLES

The invention will be further illustrated by means of the following non-limiting examples.

Example 1

According to the Invention

Catalyst Preparation

Different catalysts, each having at least one hydrogenating metal supported on a silica-bound acidic zeolite beta, were prepared via an incipient wetness impregnation procedure. Particles (30-80 mesh) of silica bound zeolite beta (50 wt % silica and 50 wt % zeolite beta; zeolite beta with a silica/alumina ratio of 200) and a pore volume of 0.61 ml/g were impregnated with different metal solutions, dried for 2 hours at 100° C. and then calcinated for two hours at 450° C. The resultant metal concentrations (wt % metal based on the total weight of the catalyst) and the metal salt used in the impregnation solutions are shown in Table 1.

Hydrogenation Process (Experiments 1 to 5)

0.5 grams of catalyst particles were loaded in an autoclave reactor. The catalyst was reduced and dried at 15 bar hydrogen pressure and 240° C. for 30 minutes. Then 7 grams of ethyl levulinate were injected into the heated reactor and reacted under 80 bar hydrogen pressure at 250° C. for 4 hours under continuous stirring (500 rpm). After 4 hours, the reaction was stopped by rapidly cooling the reactor to a temperature below 10° C. The composition of the reaction product was determined with gas chromatography. The mole % (based on moles ethyl levulinate supplied to the reactor) of unconverted ethyl levulinate, gamma valerolactone and the sum of ethyl pentanoate and pentanoic acid are given in Table 1.

Example 2

Comparison

Catalyst Preparation

Similar catalysts as described in EXAMPLE 1 were prepared with a catalyst support of silica only (no zeolite beta). The pore volume of the silica was 0.95 ml/g. The resultant metal concentrations (wt % metal based on the total weight of the catalyst) and the metal salt used in the impregnation solutions are shown in Table 1.

Hydrogenation Process (Experiments 6 to 10)

Ethyl levulinate was hydrogenated as described in EXAMPLE 1 with the catalysts comprising a hydrogenating metal on silica only (without zeolite beta). The composition of the reaction product is given in Table 1.

Example 3

Hydrogenation Process (Experiments 11 to 16)

Hydrogenation experiments were carried out as described in EXAMPLE 1. As reactant, 7 grams of lactone were injected into the heated reactor. In experiments 11, 12 and 14 to 16, ethanol in an amount such that the lactone to ethanol molar ratio is 1.0 was also injected into the reactor. Different lactones were used as reactants in different experiments. In experiments 11 to 14, γ-valerolactone was used as reactant; in experiment 15, δ-hexanolactone was used as reactant; in experiment 16 (not according to the invention), gamma butyrolactone (γ-butyrolactone) was used as reactant Gamma butyrolactone is a lactone that is not substituted at the ring-closing carbon atom. The catalysts were prepared as described in EXAMPLE 1. The resultant metal concentrations (wt % metal based on the total weight of the catalyst) and the metal salt used in the impregnation solutions are shown in Table 2. In experiment 14 (not according to the invention), a commercially available catalyst comprising nickel on silica was used (KL6564 ex. Kataleuna). The mole % (based on moles lactone supplied to the reactor) of unconverted lactone and the sum of the moles of saturated ethyl ester and saturated acid formed are given in Table 2. In experiment 13 (no ethanol), only acid was formed.

TABLE 1

Catalyst composition and composition of reaction product for the hydrogenation of ethyl levulinate without external alcohol

| experiment | metal | support | EL[a] | γVL[b] | ethyl pentanoate/ pentanoic acid |
|---|---|---|---|---|---|
| 1 | 10 wt % Ni/ 0.1 wt % Pt | zeolite β/ silica | 2 | 1 | 60 |
| 2 | 10 wt % Re/ 0.1 wt % Pt | zeolite β/ silica | <1 | 11 | 60 |
| 3 | 1 wt % Rh | zeolite β/ silica | 1 | 22 | 74 |
| 4 | 1 wt % Ru | zeolite β/ silica | 6 | 2 | 62 |
| 5 | 1 wt % Pd | zeolite β/ silica | 5 | 2 | 47 |
| 6 | 10 wt % Ni/ 0.1 wt % Pt | silica | 3 | 77 | 2 |
| 7 | 10 wt % Re/ 0.1 wt % Pt | silica | <1 | 68 | 2 |
| 8 | 1 wt % Rh | silica | 63 | 18 | <1 |
| 9 | 1 wt % Ru | silica | 23 | 54 | 1 |
| 10 | 1 wt % Pd | silica | 72 | 5 | 2 |

[a]EL: unconverted ethyl levulinate
[b]γVL: gamma valerolactone
metal salts used for catalyst preparation:
experiments 1 and 6: $Ni(NO_3)\cdot 6H_2O/Pt(NH_3)_4(NO_3)_2$
experiments 2 and 7: $HReO_4/Pt(NH_3)_4(NO_3)_2$
experiments 3 and 8: $Rh(NO_3)_3$
experiments 4 and 9: Ru-nitrosylnitrate
experiments 5 and 10: $Pd(NH_3)_4(NO_3)_2$

TABLE 2

Catalyst composition and composition of reaction product for the hydrogenation of lactones (experiments 11 to 16)

| experiment | metal | support | reactant lactone | ethanol | unconverted lactone (mole %) | ethyl ester/ acid (mole %) |
|---|---|---|---|---|---|---|
| 11 | 10 wt % Ni/0.1 wt % Pt | zeolite β/silica | γVL[a] | + | 23 | 65[d] |
| 12 | 1 wt % Pt | zeolite β/silica | γVL[a] | + | 5 | 71[d] |
| 13 | 10 wt % Ni/0.1 wt % Pt | zeolite β/silica | γVL[a] | − | 32 | 46[e] |

TABLE 2-continued

Catalyst composition and composition of reaction product for the hydrogenation of lactones (experiments 11 to 16)

| experiment | metal | support | reactant lactone | ethanol | unconverted lactone (mole %) | ethyl ester/ acid (mole %) |
|---|---|---|---|---|---|---|
| 14 | Ni | silica | γVL[a] | + | 92 | 3[d] |
| 15 | 10 wt % Ni/0.1 wt % Pt | zeolite β/silica | δHL[b] | + | 3 | 81[f] |
| 16 | 10 wt % Ni/0.1 wt % Pt | zeolite β/silica | γBL[c] | + | 46 | 1[g] |

[a]γVL: gamma valerolactone
[b]δHL: delta hexanolactone
[c]γBL: gamma butyrolactone
metal salts used for catalyst preparation:
experiments 11, 12, 15 and 16: $Ni(NO_3)\cdot 6H_2O/Pt(NH_3)_4(NO_3)_2$
experiment 13: $Pt(NH_3)_4(NO_3)_2$
[d]ethyl pentanoate and pentanoic acid
[e]only pentanoic acid
[f]ethyl hexanoate and hexanoic acid
[g]ethyl butanoate and butanoic acid

Example 4

Preparation of Mixture of Levulinic Acid Dimers

Dimers of levulinic acid were prepared as follows: A reactor was filled with 26.6 g of beads of an industrial grade palladium-doped strongly acidic catalyst (AMBERLYST® CH 28, ex. Rohm and Haas Company). The catalyst comprised 0.7 wt % Pd on a macroreticular, sulphonic acid, styrene di vinyl benzene co-polymer. The empty space above the catalyst bed was filled with 0.8 mm diameter silicon carbide particles. Catalyst and silicon carbide particles were fixed between balls of ceramic wool. The reactor was pressurised with hydrogen to a pressure of 20 bar g and brought to a temperature of 130° C. An organic phase comprising 98 wt % levulinic acid was then fed to the reactor at a weight hourly velocity of 0.3 g/g catalyst/h and hydrogen was fed to the reactor at a hydrogen/organic phase ratio of 1.5 L hydrogen per gram organic phase (hydrogen/levulinic acid molar ratio is 7.9).

Effluent was recovered from the reactor and distilled to remove unconverted levulinic acid (approximately 65 wt % of the effluent). The resulting dimer mixture contained approximately 70 wt % 4-methyl-6-oxononanedioic acid and approximately 30 wt % other levulinic acid dimers (including the ones according to molecular formulas (6) to (9).

Hydrogenation Process 1.5 grams of catalyst particles of a catalyst comprising 10 wt % Ni and 0.1 wt % Pt on silica-bound zeolite beta (the catalyst is prepared as described above for EXAMPLE 1) was loaded in an autoclave reactor. The catalyst was reduced and dried as described above for EXAMPLE 1. 3.2 grams of the mixture of dimers of levulinic acid, prepared as described above, was diluted with ethanol (molar ratio ethanol-to-levulinic acid dimers was 5.0), the ethanol/dimer mixture was pre-heated to 200° C. and injected into the reactor. The dimers were then reacted under 80 bar hydrogen pressure at 240° C. for 75 hours under continuous stirring (500 rpm). The reaction was stopped by rapidly cooling the reactor to a temperature below 10° C. NMR analysis of the product showed that the carbonyl groups had disappeared and that no lactone groups were formed.

What is claimed is:

1. A process for preparing a compound selected from the group consisting of:

dialkyl 4-methylnonanedioate:

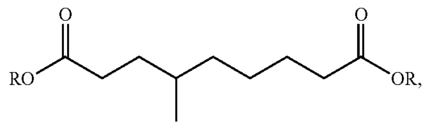

dialkyl 3-ethyl-4-methylheptanedioate:

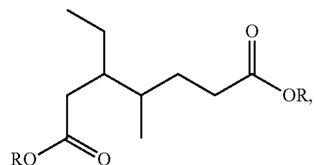

and a combination thereof, wherein R is an alkyl group having at most 10 carbon atoms, which comprises, reacting γ-valerolactone, δ-hexanolactone, levulinic acid, or a dimer of levulinic acid or an ester of levulinic acid in the presence of hydrogen and an alkyl alcohol having at most 10 carbon atoms with an acidic heterogeneous catalyst that comprises an acidic zeolite and a hydrogenating metal, at a temperature in the range of from 100 to 350° C. and a pressure in the range of from 1 to 150 bar (absolute) under conditions effective to produce the compound.

2. The process of claim 1, wherein the alkyl alcohol is ethanol, and the compound produced is diethyl-4-methylnonanedioate, diethyl 3-ethyl-4-methylheptanedioate, or a combination thereof.

3. The process of claim 1, wherein the alkyl alcohol is a diol selected from the group consisting of ethylene glycol and butane-1,4-diol.

4. The process of claim 1, wherein the dimer of levulinic acid is selected from the group consisting of:

4-methyl-6-oxononanedioic acid:

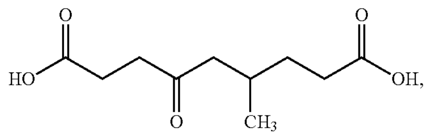

3-acetyl-4-methylheptanedioic acid:

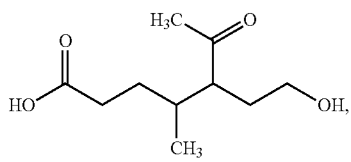

5-(2-methyl-5-oxotetrahydrofuran-2-yl)-4-oxopentanoic acid:

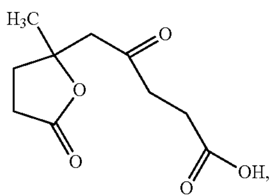

and 3-(2-methyl-5-oxotetrahydrofuran-2-yl)-4-oxopentanoic acid:

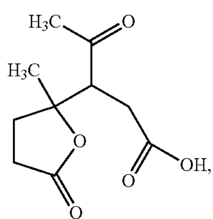

or a combination of two or more thereof.

5. The process of claim 1, wherein the catalyst comprises a physical mixture of an acidic zeolite and a supported hydrogenating metal.

6. The process of claim 1, wherein the catalyst further comprises a binder selected from the group consisting of silica, alumina, acidic clay, titania and zirconia.

* * * * *